United States Patent [19]

Wakamura

[11] Patent Number: 5,030,843
[45] Date of Patent: Jul. 9, 1991

[54] APPARATUS FOR MEASURING PARTICLES IN LIQUID HAVING A LAMINAR FLOW CONDITION

[75] Inventor: Hitoshi Wakamura, Hino, Japan
[73] Assignee: Kowa Company Ltd., Japan
[21] Appl. No.: 478,694
[22] Filed: Feb. 12, 1990
[30] Foreign Application Priority Data Feb. 13, 1989 [JP] Japan .................................. 64-31120

[51] Int. Cl.⁵ ............................................. G01N 15/06
[52] U.S. Cl. .................................... 250/574; 356/339
[58] Field of Search ....................... 250/574, 575, 576; 356/337, 338, 339, 340, 341, 342, 343

[56] References Cited

U.S. PATENT DOCUMENTS

| | | | |
|---|---|---|---|
| 4,110,043 | 8/1978 | Eisert | 356/337 |
| 4,200,802 | 4/1980 | Salzman et al. | 356/343 |
| 4,746,215 | 5/1988 | Gross | 356/339 |
| 4,830,494 | 5/1989 | Ishikawa et al. | 356/339 |

Primary Examiner—David C. Nelms
Assistant Examiner—Que T. Le
Attorney, Agent, or Firm—Bruce L. Adams; Van C. Wilks

[57] ABSTRACT

An apparatus for measuring particles in liquid in which a laser beam is projected into the liquid containing particles to be measured which are caused to flow into a measurement zone in a measuring cell, and light scattered from the particles passing through the measurement zone is received by the light receiving means to measure characteristics of the particles. The light receiving means is disposed with its optical axis nearly perpendicular to the axis of projection of laser light. The measuring cell has inlet and outlet liquid passages communicating with the measurement zone, the liquid passages having cylindrical portions which communicate through inclined portions with the measurement zone to assure a laminar flow of the liquid through the measurement zone.

10 Claims, 3 Drawing Sheets

APPARATUS FOR MEASURING PARTICLES IN LIQUID HAVING A LAMINAR FLOW CONDITION

BACKGROUND OF THE INVENTION

1. Field of the Invention

This invention relates to an apparatus for measuring particles in liquid, and more particularly to an apparatus for measuring particles in liquid in which a laser beam is projected into a flowing liquid and light scattered from particles present in the liquid is evaluated to measure particle size, number of particles and other characteristics of the particles.

2. Description of the Prior Art

The prior art includes techniques in which light is projected into a measurement zone and the amount of transmitted light, scattering characteristics and the like are measured to determine the size, number and other characteristics of particles in the zone.

For example, while this technique is employed in monitoring particulate impurities in pure water, since such particles in pure water tend to be small and present in low concentrations, the particles are difficult to monitor. For this reason, in order to increase the intensity of light scattered from particles, an incident beam from a laser light source or the like is conventionally collected in a small zone, creating a measurement zone of high light intensity in the measurement cell, and then the scattered light from particles passing through this zone is received (see, for example U.S. Pat. No. 4,830,494).

In a particle measurement apparatus which projects laser light at particles and analyzes light scattered from the particles, the direction from which light scattered from the particles is received is important as is the shape of the measurement section through which the particles pass in the measurement cell. Because the distribution of laser light intensity exhibits a Gaussian distribution, conventional apparatus for measuring particles in liquid employs a "90-degree lateral light receiving system" in which light scattered from particles illuminated with laser light is received in a direction nearly perpendicular to the axis of projection of the laser beam in order to improve the efficiency of particle measurement.

This system employs an arrangement in which the direction of particle travel is colinear with the optical axis of a light receiving lens or in which the direction of particle travel lies in the plane defined by the optical axis of the laser and the optical axis of the light receiving lens and crosses the optical axis of the light receiving lens at an angle in the range of 20-70 degrees. Slits are disposed on the imaging surface of the light receiving lens so that scattered light from the particles which pass through areas of high light intensity is selectively received to obtain good particle size resolution.

Furthermore, in order to force particles to travel in a specific direction through measurement cells employing this sort of system, there are methods in which sheath flow is employed to establish cylindrical flow through the measurement zone, and methods in which a stirrer is used with a cylindrical wall to establish a rotating flow.

In the above method using sheath flow, the high rate of flow required to establish the cylindrical flow becomes a problem. The method using rotating flow, on the other hand, disadvantageously has the lack of a way of verifying that liquid in the cylindrical section is adequately circulated through the inlet and outlet pipes in the cell with the cylindrical section used to establish the rotating flow, and has the possibility that the same particle would repeatedly pass through the measurement zone.

As described above, when forcing particles to travel in a certain direction through the measurement zone, if the flow of particles assumes a turbulent flow state rather than a laminar flow state, the direction of travel of particles cannot be set to a direction along the optical axis of the light receiving lens or to a direction parallel to the plane defined by the optical axis of the laser and the optical axis of the light receiving lens, so that good particle resolution cannot be obtained.

SUMMARY OF THE INVENTION

Therefore, an object of the present invention is to solve these problems and provide an apparatus for measuring particles in liquid which can effectively receive scattered light from particles and perform accurate measurement of particles.

According to the invention, there is provided an apparatus for measuring particles in liquid in which a laser beam is projected into the liquid containing particles to be measured which are caused to flow into a measurement zone, and light scattered from the particles passing through the measurement zone is received to measure characteristics of the particles. The apparatus in the invention comprises a laser source for producing the laser beam, a laser projector for projecting the laser beam into the measurement zone, light receiving means disposed with its optical axis nearly perpendicular to the axis of projection of the laser beam for laterally receiving light scattered from the particles, a measuring cell for causing the liquid containing the particles to flow into the measurement zone in a direction along the optical axis of the light receiving means, and means disposed in the measuring cell for forming laminar flow in the measurement zone.

Preferably, the measuring cell includes inlet pipes disposed symmetrically with respect to the optical axis of the light-receiving means and each having a first portion for causing the liquid to flow into the measurement cell at an angle nearly perpendicular to the optical axis of the light receiving means and a second portion communicating with the first portion and extending nearly parallel thereto. The measuring cell further includes a cylindrical portion which communicates with the second portion of the inlet pipes and extends along the optical axis of the light receiving means through the measurement zone. The second portion of the inlet pipes forms a double cylindrical portion which is coaxial with the cylindrical portion.

The diameter of the double cylindrical portion is preferably set to be equal to or greater than that of the cylindrical portion, and the diameter of the first portion of the inlet pipes is set to be smaller than that of the cylindrical portion.

The measuring cell further includes outlet pipes communicating with the cylindrical portion for discharging the fluid to the outside. The outlet pipes and inlet pipes are disposed symmetrically with respect to the optical axis of projection of the laser beam.

In the measurement cell used in the invention, Teflon or other corrosion-resistant material is used on the areas in contact with the liquid, and the inlet and outlet pipes for the liquid are disposed at points which are symmetrical with respect to the optical axis of the light receiving lens so that the liquid flows in the direction of the optical axis of the light receiving lens.

A sharp increase in the sectional area of flow near the inlet pipe tends to cause turbulent flow. To prevent this, a double cylindrical section is used to smooth out the flow of liquid flowing in the direction normal to the optical axis of the light receiving lens, and a cylindrical section is also used to force particles passing through the measurement zone to travel at a fixed speed. Both the sections are formed so that there is no sharp change in sectional area between them. Furthermore, in the measurement cell of the invention, entrance and exit windows for the laser beam are formed on the sides of the cylindrical section along with a window for receiving scattered light from particles in the liquid and a transparent window formed in a position opposite to the light receiving window to prevent reflections from the wall surface.

With a measurement cell of such configuration, particles in the measurement zone of the measurement cell flow in a laminar flow pattern, so stability of the particle flow in the direction of travel may be attained in a short distance.

BRIEF DESCRIPTION OF THE DRAWINGS

The objects and features of the present invention will become more apparent from the following detailed description taken in conjunction with the accompanying drawings, in which.

DETROIT DESCRIPTION OF PREFERRED EMBODIMENTS

The invention will now be described in detail based on a preferred embodiment.

Figure 1:
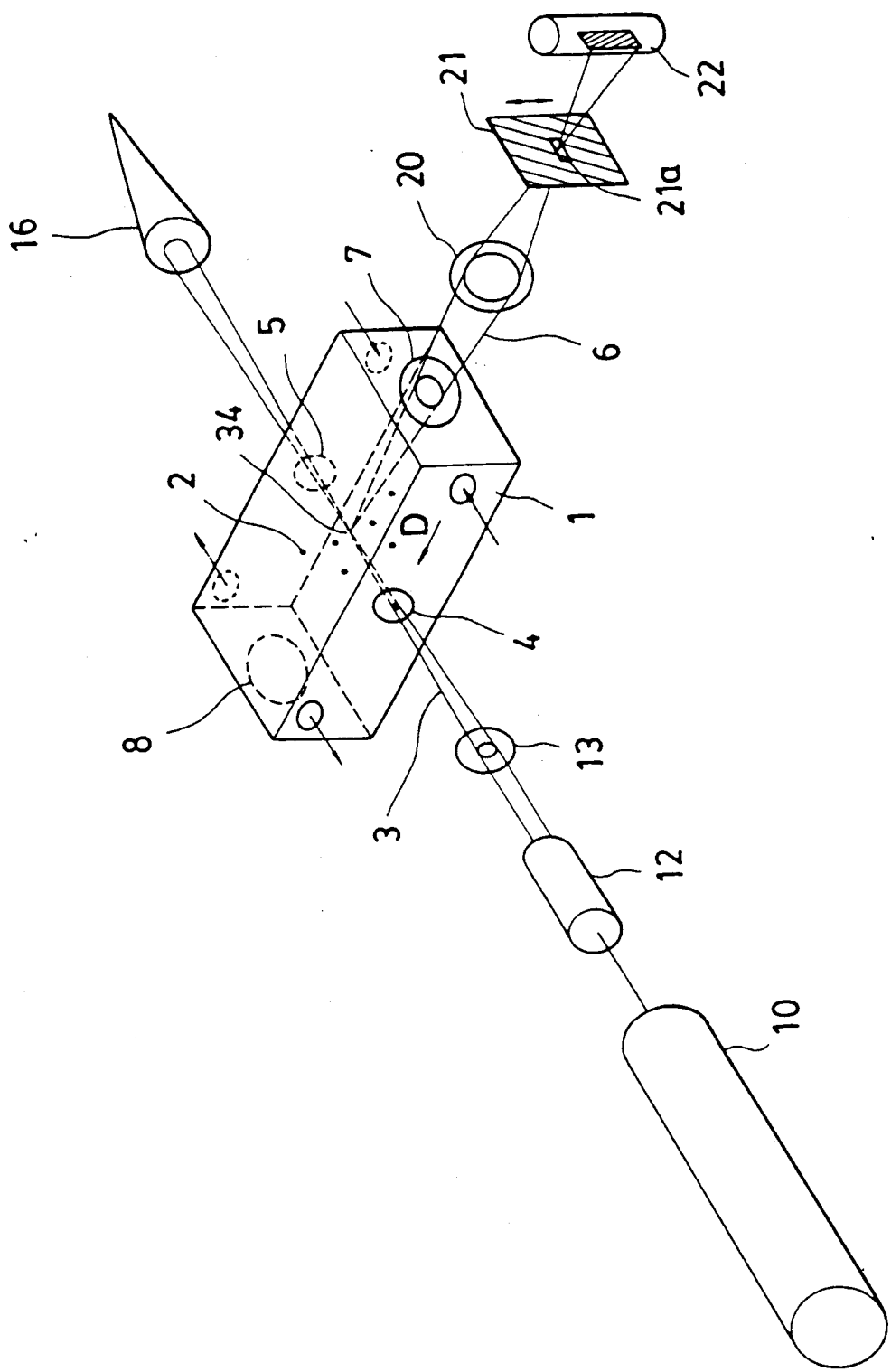
FIG. 1 is a perspective view showing an arrangement of an apparatus of the invention for measuring particles in liquid.

In FIG. 1, reference number 1 denotes a measurement cell into which a sample such as pure water or the like containing particles 2 to be measured is caused to flow as described hereafter.

An incident laser beam 3 obtained from a laser light source 10 constituted by a helium-neon laser or the like is projected through a laser projection optical system onto the particles 2. The laser projection optical system is constituted by a beam expander 12 which expands the laser beam coming from the laser light source 10 and a condenser 13.

The laser beam 3 from the condenser 13 is focused through an entrance window 4 formed in the measurement cell 1 at a focal point 34 which forms the center of the measurement zone. Then the laser beam exits from an exit window 5 and is absorbed by a light-absorbing trap 16.

As described hereafter, a light receiving lens 20 disposed in a direction nearly perpendicular to the axis of projection of the laser is used to form an image of laser light scattered laterally from the particles 2 on a mask 21. A slit 21a is formed on the mask 21 so that scattered light limited by the slit 21a reaches a photomultiplier tube 22. The signal obtained from the photomultiplier tube 22 is provided as input to a signal processor (not shown) in which well-known methods of photon-counting are used to measure particle characteristics such as the particle distribution, particle size and the like.

Figure 2:
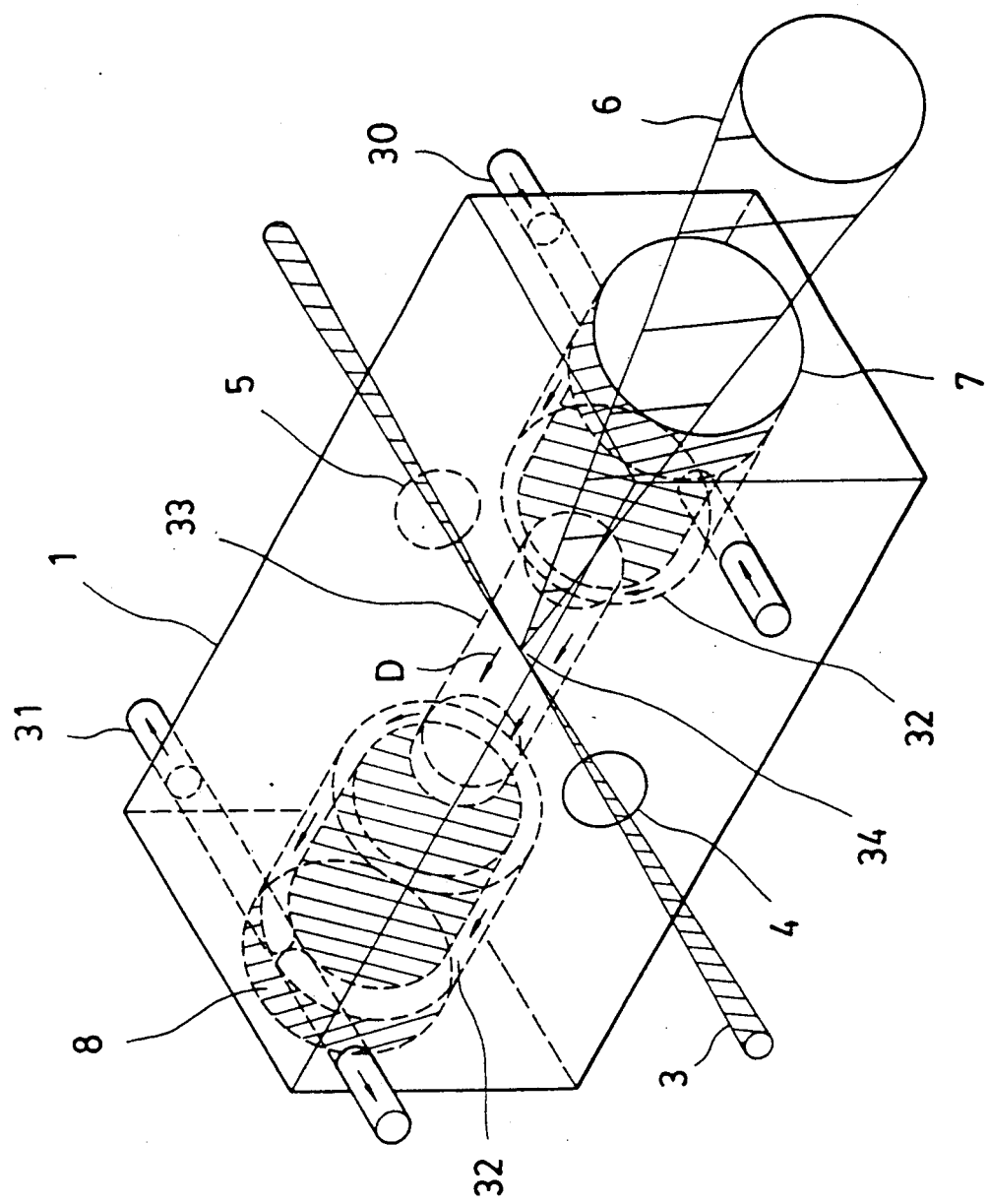
FIG. 2 is an enlarged perspective view of a portion of the measuring cell of the apparatus in FIG. 1.
Figure 3:
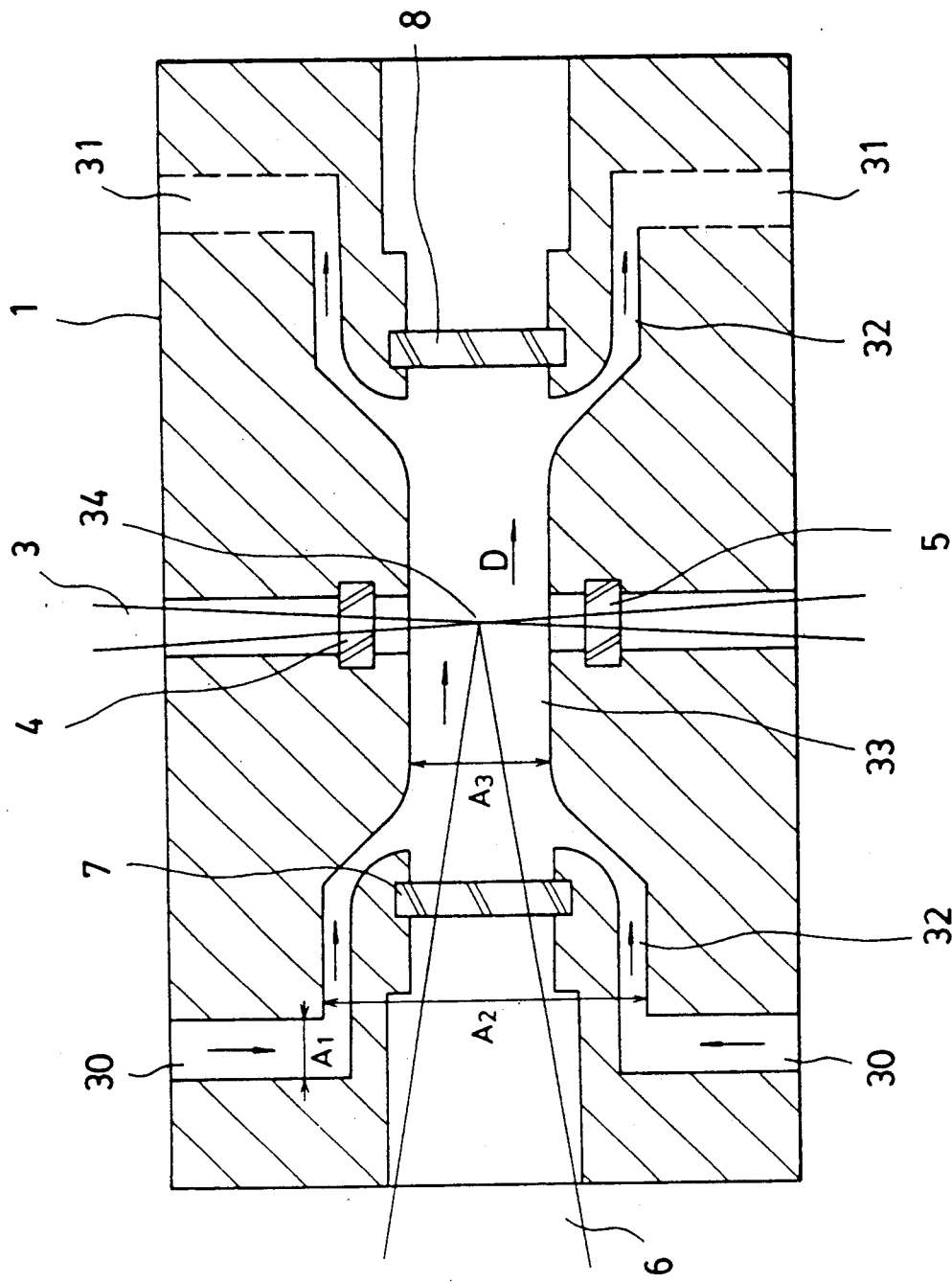
FIG. 3 is a top view of the measuring cell of the same apparatus in a cross-section along a plane containing the axis of projection of the laser and the optical axis along which scattered light is received.

In addition, as shown in detail on FIGS. 2 and 3, the measurement cell 1 is provided with a cylindrical section 33 which acts as a measurement zone centered around the focal point 34. Disposed on the periphery of this cylindrical section 33 are an entrance window 4 into which the laser beam 3 from the laser light source 10 enters, an exit window 5 through which the laser beam 3 exits, and a light receiving window 7 which receives scattered light 6 from particles 2 passing through the focal point 34. Furthermore, an anti-reflection window 8 is provided at a location opposite the light receiving window 7 on the other side of the focal point 34 to reduce the amount of reflected light which enters the light receiving optical system. Behind the exit window 5 is disposed the light-absorbing trap 16 which absorbs the laser beam as described above with reference to FIG. 1.

In addition, the cylindrical section 33 of the measurement cell 1 is provided with an inlet passage comprised of inlet pipes 30 through which a liquid containing particles 2 flows into the measurement cell 1. These inlet pipes 30, as shown in detail on FIG. 3, enter the measurement cell 1 from each side at an angle nearly perpendicular to the optical axis of the light receiving lens 20, then bend to form portions that lie nearly parallel to the optical axis of the light receiving lens 20 and connect through inwardly inclined portions to the cylindrical section 33 at the light receiving window 7. Thus a double cylindrical section 32 is formed in the liquid inlet section of the measurement cell, so that a sample liquid flows in through this double cylindrical section 32. Furthermore, an outlet passage comprised of outlet pipes 31 which discharge the sample liquid are disposed such that their locations and those of the inlet pipes 30 are symmetrical with respect to the axis of projection of the laser beam, and these outlet pipes 31 are formed in the same manner as the inlet pipes 30 so that a double cylindrical section 32 is also formed in the liquid outlet section.

These double cylindrical sections 32 are disposed concentrically with the cylindrical section 33, and the double cylindrical sections 32 and cylindrical section 33 form conical surfaces centered about an extension of the center line between them. Therefore, in the measurement cell used in the invention, both the liquid inlets 30 are disposed symmetrically with respect to the optical axis of the light receiving lens 20 so that the liquid will flow in the direction of the optical axis of the light receiving lens, and thus the direction of flow of particles is nearly parallel to the optical axis of the optical system which receives scattered light from the particles.

Note that in the measurement cell used in this preferred embodiment, Teflon or other corrosion-resistant material is used on the areas in contact with the liquid.

Now the operation of an apparatus of such configuration will be described.

A laser beam from the laser light source 10 passes through the beam expander 12 and condenser 13 to enter the entrance window 4 of the measurement cell and is focused at the focal point 34 in the measurement zone.

At the same time, a sample liquid containing particles flows through the inlet pipes 30 and double cylindrical section 32 into the cylindrical section 33, or measurement zone, of the measurement cell 1. Since the two inlet pipes 30 are disposed symmetrically about and lie in directions normal to the double cylindrical section 32, the sample liquid is mixed to homogeneity in the double cylindrical section 32. In this case, if the combined sectional area $2A_1$ of the two inlet pipes 30 each of sectional area A, sectional area $A_2$ of the double cylindrical section 32, and sectional area $A_3$ of the cylindrical section 33 are related by the relation $2A_1 < < A_2 > = A_3$, the change in sectional area between the double cylindrical section and the cylindrical section is reduced so that the sample liquid whose flow is smoothed by a ring-shaped cross section in the double cylindrical section will not assume a turbulent flow state when flowing into the cylindrical section 33, but rather becomes a cylindrical flow of virtually unchanged sectional area just before entering the measurement zone and thus passes through the measurement zone in laminar flow at a constant speed nearly perpendicular to the optical axis of the laser.

Laser light is scattered by particles 2 passing through the measurement zone in this manner. The light receiving lens 20 forms an image on the mask 21 of that portion of the scattered light 6 which is scattered laterally in a direction perpendicular to the optical axis of the laser. The scattered light 6 then reaches the photomultiplier tube 22. The signal obtained from the photomultiplier tube 22 is provided as an input to a signal processor in which well-known methods of photon-counting are used to measure particle characteristics such as the particle distribution, particle size and the like.

After the sample liquid passes through the measurement zone, it is discharged to the outside through the outlet pipes 31. These outlet pipes 31 are disposed to the rear or downstream of the cylindrical section so that the effect of wake is ameliorated. Care is taken to dispose the two outlet pipes 31 in the top portion of the double cylindrical section so that any air bubbles trapped within the cell are swiftly discharged, preventing air from being retained in the cell.

Note that in FIGS. 1, 2 and 3, the symbol D indicates the direction of flow.

As described above, in the present invention, a light receiving means for receiving laterally scattered light is disposed in a direction nearly perpendicular to the optical axis of the laser, and the liquid containing particles is forced to flow in a direction nearly parallel to the optical axis of the scattered light receiving lens, while the liquid flow can reliably form a stable laminar flow in a short distance in the measurement zone, so that particle size distribution measurements can be made under optimal conditions.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for measuring particles in liquid in which a laser beam is projected into the liquid containing particles to be measured which are caused to flow into a measurement zone, and light scattered from the particles passing through the measurement zone is received to measure characteristics of the particles, comprising;

a laser source for producing the laser beam;

a laser projector for projecting the laser beam into the measurement zone;

light receiving means disposed with its optical axis nearly perpendicular to the axis of projection of the laser beam for laterally receiving light scattered from the particles; and a measuring cell defining the measurement zone and for causing the liquid containing the particles to flow into the measurement zone in a direction along the optical axis of the light receiving means in a laminar flow condition, the measurement cell comprising inlet pipes disposed symmetrically with respect to the optical axis of the light receiving means and each having a first portion for causing the liquid to flow into the measurement cell at an angle nearly perpendicular to the optical axis of the light receiving means and a second portion communicating with the first portion and extending nearly parallel thereto, and a cylindrical portion which communicates with the second portion of the inlet pipes and extends along the optical axis of the light receiving means through the measurement zone, the second portion of the inlet pipes forming a double cylindrical portion which is coaxial with the cylindrical portion.

2. An apparatus as set forth in claim 1, wherein the diameter of the double cylindrical portion is set to be equal to or greater than that of the cylindrical portion.

3. An apparatus as set forth in claim 1 or 2, wherein the diameter of the first portion of the inlet pipes is set to be smaller than that of the cylindrical portion.

4. An apparatus as set forth in claim 1 or 2 or 3, wherein the measuring cell further comprises outlet pipes communicating with the cylindrical portion for discharging the fluid to the outside, the outlet pipes and inlet pipes being disposed symmetrically with respect to the optical axis of the light receiving means.

5. An apparatus for measuring particles in a liquid, comprising: a measuring cell having means therein defining an elongate measurement zone having a longitudinal axis, and means for flowing a liquid containing particles to be measured lengthwise through the measurement zone in a laminar flow condition comprising inlet passage means having an upstream portion extending generally parallel to the longitudinal axis and a transition portion inclined inwardly from the upstream portion to the upstream end of the measurement zone and outlet passage means having a downstream portion extending generally parallel to the longitudinal axis and a transition portion inclined outwardly from the downstream end of the measurement zone to the downstream portion whereby the liquid flows into the measurement zone through the inlet passage means and flows out of the measurement zone through the outlet passage means; means for projecting a beam of laser light into the measurement zone to cause particles in the liquid to scatter the laser light; and light-receiving means for receiving light scattered by the particles for use in measuring a property of the particles.

6. An apparatus according to claim 5; wherein the light-receiving means is positioned to receive light scattered along the longitudinal axis of the measurement zone.

7. An apparatus according to claim 6; wherein the light-receiving means has an optical axis for receiving therealong the scattered light, the optical axis being transverse to the direction of projection of the beam of laser light through the measurement zone.

8. An apparatus according to claim 5; wherein the measurement zone has a cylindrical shape.

9. An apparatus according to claim 8; wherein the upstream portion of the inlet passage means and the downstream portion of the outlet passage means each have at least a partly ring shape coaxial with the cylindrical measurement zone.

10. An apparatus according to claim 5; wherein the measurement zone has a linear longitudinal axis.

* * * * *